(12) United States Patent
Hirt et al.

(10) Patent No.: US 10,473,646 B2
(45) Date of Patent: Nov. 12, 2019

(54) IN VITRO CULTURING OR EXPANDING HUMAN OR ANIMAL TISSUE

(71) Applicants: UNIVERSITAETSSPITAL BASEL, Basel (CH); CELLEC BIOTEK AG, Basel (CH)

(72) Inventors: Christian Hirt, Basel (CH); Adam Papadimitropoulos, Basel (CH); Giandomenica Iezzi, Basel (CH); Volker Lorber, Vienna (AT); Manuele Giuseppe Muraro, Basel (CH)

(73) Assignees: UNIVERSITAETSSPITAL BASEL, Basel (CH); CELLEC BIOTEK AG, Basel (CH)

( * ) Notice: Subject to any disclaimer, the term of this patent is extended or adjusted under 35 U.S.C. 154(b) by 155 days.

(21) Appl. No.: 15/314,245

(22) PCT Filed: May 26, 2015

(86) PCT No.: PCT/EP2015/061614
§ 371 (c)(1),
(2) Date: Nov. 28, 2016

(87) PCT Pub. No.: WO2015/181185
PCT Pub. Date: Dec. 3, 2015

(65) Prior Publication Data
US 2019/0018002 A1      Jan. 17, 2019

(30) Foreign Application Priority Data

May 26, 2014   (EP) .................................... 14169901

(51) Int. Cl.
*G01N 33/50* (2006.01)
*A01N 1/02* (2006.01)
(Continued)

(52) U.S. Cl.
CPC ....... *G01N 33/5082* (2013.01); *A01N 1/0247* (2013.01); *C12N 5/0068* (2013.01);
(Continued)

(58) Field of Classification Search
None
See application file for complete search history.

(56) References Cited

U.S. PATENT DOCUMENTS

| | | | | |
|---|---|---|---|---|
| 2002/0009805 A1* | 1/2002 | Nevo | .................. | A61L 27/3604 435/366 |
| 2009/0023127 A1* | 1/2009 | Yu | ........................... | A01N 1/02 435/1.2 |
| 2015/0079584 A1* | 3/2015 | Gevaert | ............ | G01N 33/5011 435/6.1 |

FOREIGN PATENT DOCUMENTS

AU    2004202491 B2    10/2006
JP    2000-509979 A    8/2000
(Continued)

OTHER PUBLICATIONS

Brattain et al, Cancer Research, May 1981, vol. 41, pp. 1751-1756. (Year: 1981).*
(Continued)

*Primary Examiner* — Allison M Fox
(74) *Attorney, Agent, or Firm* — Medler Ferro Woodhouse & Mills PLLC

(57) ABSTRACT

The invention relates to a method of in vitro culturing or expanding human or animal tissue (2, 2'). The method comprises: obtaining a sample of human or animal tissue; downsizing tissue (21, 21') of the sample; generating an assembly by placing the downsized tissue on a scaffold or hydrogel (22, 22'); arranging the assembly inside a culture chamber of a 3D perfusion system (23, 23'); and perfusing the assembly in the 3D perfusion system for a predefined time (24, 24'). The method according to the invention allows (Continued)

for preparing and directly culturing in vitro fresh tissue specimens for a high efficient in vitro culturing using a perfused bioreactor system. As single cells of tissue are in most cases undergoing to an in vitro cell-death due to missing micro environmental signals, the use of downsized tissue, comprising cell clumps and tissue fragments of hundreds of cells, may help to prevent cell death in vitro as well as to maintain the initial heterogeneous tissue microenvironment consisting of specific cell types such as epithelial, stromal and immune cells together. Thus, the method according to the invention is capable of efficiently culturing the whole tissue over time, thus allowing for survival of original cell types.

18 Claims, 9 Drawing Sheets
(9 of 9 Drawing Sheet(s) Filed in Color)

(51) Int. Cl.
  *C12N 5/00* (2006.01)
  *C12N 5/09* (2010.01)
(52) U.S. Cl.
  CPC ........ *C12N 5/0693* (2013.01); *C12N 2513/00* (2013.01); *C12N 2533/54* (2013.01); *G01N 2500/10* (2013.01)

(56) References Cited

FOREIGN PATENT DOCUMENTS

| WO | 97/39624 A1 | 10/1997 |
|---|---|---|
| WO | 01/48153 A1 | 7/2001 |
| WO | 2010/035049 A1 | 4/2010 |
| WO | 2013/182574 A1 | 12/2013 |

OTHER PUBLICATIONS

"Scaffold.";Medical Dictionary. 2009. Farlex and Partners Jun. 28, 2019;https://medical-dictionary.thefreedictionary.com/scaffold (Year: 2009).*
Ternullo et al, European Journal of Pharmaceutical Sciences, 2017; vol. 96, pp. 334-341. (Year: 2017).*
Rambini et al, Journal of Neuroscience Methods, 2009, vol. 180, pp. 243-254. (Year: 2009).*
Fischbach et al, Nature Methods, 2007, vol. 4, No. 10, pp. 855-860. (Year: 2007).*
Fischbach et al, PNAS 2009, vol. 106, No. 2, pp. 399-404 (Year: 2009).*
Fong et al, PNAS, 2013, vol. 110, No. 16, pp. 6500-6505. (Year: 2013).*
International Preliminary Report on Patentability for International Application No. PCT/EP2015/061614, dated Nov. 29, 2016.
Written Opinion of the International Searching Authority for International Application No. PCT/EP2015/061614, dated Aug. 17, 2015.
International Search Report for International Application No. PCT/EP2015/061614, dated Aug. 17, 2015.
Bourgine, P et al. "Engineering of Cell-Free Osteo-Inductive Bone Graft Substitutes in 3D Perfusion Bioreactors Using a Death-Inducible hMSC Line," Oral Presentations, Journal of Tissue Engineering and Regenerative Medicine, vol. 8, Suppl. s1, pp. 39-206. Jun. 1, 2014.
Partial Translation of Journal Juzen Medical Society (1975) 84:548-561.
Notice of Reasons for Rejection issued in Japanese Application No. 2017-514951, dated Mar. 26, 2019.

* cited by examiner

A

B

IN VITRO CULTURING OR EXPANDING HUMAN OR ANIMAL TISSUE

TECHNICAL FIELD

The present invention relates to a method of in vitro culturing or expanding human or animal tissue, a method of testing efficacy of tumor or cancer treatment using such a culturing or expanding method and a method of enriching cells of a cell type from human or animal tumor tissue using such a culturing or expanding method.

BACKGROUND ART

In recent years, scientific evidence proving the inadequacy of monolayer cell cultures has triggered the development of techniques allowing culture of cells in a three-dimensional (3D) environment. These techniques include the use of suitable porous biomaterials, i.e. scaffolds, that can be seeded with cells but can also comprise cell clusters, tissue or tissue like structures, biopsies and similar. For example, static in vitro cultures of tumor specimens from epithelial tumors, such as colorectal cancer, have been established, allowing survival and expansion of primary tissue, although to a very limited extent.

As a consequence, tools have been made available to respond to specific needs inherent to these techniques. Among these tools, bioreactors provide a controlled chemo-physical environment suitable for the culturing of cells in 3D. In particular, perfusion bioreactors have proven to be effective in overcoming typical limitations of static cultures. Such limitations include lack of a uniform cell seeding through the scaffold, limited mass transport, i.e. nutrient delivery and waste removal, particularly in a central part of the scaffold.

In this context, WO 2013/182574 A1 presents a 3D perfusion bioreactor and system allowing for a convenient operation and handling within efficient human or animal tissue cell culturing. Beyond others, nutrient availability and oxygen delivery can be increased by using such a 3D perfused bioreactor system.

However, specific cell lines, such as cancer cell lines, being widely used for preclinical studies only marginally reflect the heterogeneity of (tumor) tissue where they derive from. They are mostly genetically homogenous with some limited morphological heterogeneity and adapted to plastic dishes through decades of in vitro cultures. A recent study compared copy-number changes, mutations and mRNA expression profiles of commonly used ovarian cancer cell lines and high-grade serous ovarian cancer tumor samples. Alarmingly, rarely used cell lines in this case resembled more closely the cognate tumor profiles than commonly used cell lines. Because of this, the translation of cell line-based studies to their patient counterparts is not always simple to perform.

The tumor microenvironment consists on cellular, e.g. stromal and immune cells, and non-cellular, e.g. extracellular matrix, components. Even characterized for their malignant invasive cell growth in vivo most cancer cells strongly depend on these factors for sustained growth in vivo as well as in vitro. Stromal and immune cells strongly influence tumor growth patterns.

In the context of colorectal cancer, it has been shown that retaining cell-cell contact increases the efficiency of generating spheroids of tumor cells from primary colorectal cancer specimens. Providing niche-dependent signals can therefore be critical for tumor cells.

On the other hand patient-derived xenograft (PDX) models, generated upon subcutaneous implantation of tumor tissue have been proposed to overcome the limitations of tumor material availability. The efficiency reported depends on the tumor type and for colorectal cancer is about 68%. Tumor growth can be observed after 1-2 months. Studies have shown that the generated tumors are more corresponding to the metastatic lesion than to the primary tumor they were derived from.

For both spheroid cell culture and patient derived xenografts the heterogeneity of the initial tumor microenvironment is lost over time, since only the epithelial cell fraction survives and expands. In the case of the PDX human stromal cells are replaced by mouse stromal cells. The initial composition is therefore drastically changed.

Therefore, there is a need for culture systems or methods allowing survival over time of whole tumor tissue, including involved cell types such as both stromal and epithelial components.

DISCLOSURE OF THE INVENTION

According to the invention this need is settled by a method of in vitro culturing or expanding human or animal tissue as it is defined by the features of independent claim 1, a method of testing efficacy of tumor or cancer treatment as it is defined by the features of independent claim 11 and by a method of enriching cells of a cell type from human or animal tumor tissue as it is defined by the features of independent claim 14. Preferred embodiments are subject of the dependent claims.

In particular, the invention deals with a method of in vitro culturing or expanding human or animal tissue comprising the steps of: obtaining a sample of human or animal tissue; downsizing tissue of the sample; generating an assembly by placing the downsized tissue on a scaffold; arranging the assembly inside a culture chamber of a 3D perfusion system; and perfusing the assembly in the 3D perfusion system for a predefined time.

Human or animal tissue can be cancer tissue and particularly colorectal cancer tissue. Further, the tissue can be glioblastoma tissue, melanoma tissue, bladder cancer tissue, prostate cancer tissue, breast cancer tissue or any other tumor tissue.

The 3D perfusion system can particularly be a 3D perfusion bioreactor such as the bioreactor described in WO 2013/182574 A1.

The term "downsizing" as used herein can particularly relate to a pre-digestion and/or a mechanical treatment of the tissue. Digested or downsized tissue can be cell clumps and tissue fragments of a plurality of cells such as ten to hundreds of cells. The tissue chunks or cell clumps may have a size of about 0.5 mm to about 2 mm such as, for example, 1 mm×1 mm. Thus, downsizing the tissue can relate to providing cell clumps and/or tissue fragments or to fragmenting the tissue.

The scaffold can be made of any suitable natural derived or synthetic material. For example it can be made of polyethylene or particularly collagen which can be comparably efficient with regard to growth and handling. The scaffold can be coated with or without extracellular matrix proteins (e.g. matrigel, etc.) and/or pre-cultured with appropriate cell sources (e.g. stromal cells etc.). Furthermore, the scaffold can be provided in a shape adapted to the shape of the culturing chamber of the bioreactor. For example, for cylindrical culturing chambers of 3D perfusion system the scaffold can preferably be disc-shaped.

For perfusing the assembly in the bioreactor a medium can be used which, e.g., can be selected from the group of: serum-free or serum-containing medium consisting of human or animal serum, patient derived plasma, pooled human serum, fetal calf serum or combinations thereof. As known from previous data autologous and human serum may be preferable since they promote the growth of both stromal and epithelial cells, whereas fetal calf serum (FCS) preferentially promotes the expansion of stromal cells. Autologous serum (AS) can be prepared by collecting a total blood sample from the tumor tissue related patient with a syringe without addition of anticoagulants; centrifuging the blood at 2600 g for 30 minutes and at 4° C.; and collecting the supernatant defined as AS. Autologous plasma (aHP) can be obtained by the same procedure but collecting blood using anticoagulants (like Heparin or EDTA).

The method according to the invention allows for increasing several fold tissue the total tissue amount, e.g., of a colorectal cancer cell line by direct perfusion in the 3D perfusion system. Based on morphological features and whole genome expression, the generated tissue-like structures can be more similar to in-vivo generated tissues such as tumors. Furthermore, their sensitivity or resistance to drug treatment is similar to that of xenografts and, e.g., even neoadjuvant treated colorectal cancer samples. The 3D perfusion system can therefore preserve important functions of the initial tumor tissue. By using small tissue chunks, i.e. the downsized tissue, the initial tumor microenvironment composition can be maintained and the integration of the tissue in the surrounding or neighboring scaffold can be allowed.

The method according to the invention allows for preparing and directly culturing in vitro fresh tissue specimens, such as colorectal cancer tumor specimens, for a high efficient in vitro culturing using a perfused bioreactor system, i.e. the 3D perfusion system. As single cells of tissue undergo in most cases cell-death due to missing micro environmental signals, the use of downsized tissue, including cell clumps and tissue fragments of hundreds of cells, may help not only to prevent cell death in vitro but to keep the initial heterogeneous tissue microenvironment consisting of specific cell types such as epithelial, stromal and immune cells.

Thus, the method according to the invention is capable of efficiently culturing the whole tumor tissue over time. It can allow an increased survival of all original cell types such as both stromal and epithelial parts of the initial tumor.

Preferably, downsizing of the tissue comprises mechanically pre-treating the tissue. Such mechanical pre-treatment can be cutting, mincing, shearing or the like and combinations thereof. Like this, the tissue can efficiently be downsized. Alternatively or additionally, downsizing of the tissue preferably comprises enzymatically pre-treating the tissue. This can provide for a further efficient downsizing of the tissue wherein a combination with the mechanical pre-treatment may be particularly beneficial.

Preferably, the method according to the invention further comprises cleaning the tissue before generating the assembly. Thereby, cleaning can be performed after downsizing the tissue or particularly before downsizing the tissue. Depending on the tissue such cleaning can be particularly beneficial. Whereas, e.g., breast tissue typically is aseptic such that no cleaning is necessary, colon tissue has bacteria such that cleaning the tissue can be useful. Thereby, cleaning the tissue preferably comprises washing the tissue. Such washing may provide for a comparably simple cleaning of the tissue. Alternatively or additionally, cleaning the tissue preferably comprises anti-septic treatment. The anti-septic treatment can, e.g., be performed with an octenidine or a preparation comprising octenidine dihydrochloride. Such anti-septic treatment allows for efficiently cleaning the tissue wherein a combination with washing may be particularly beneficial.

Preferably, generating the assembly comprises arranging a grid on one side and a further grid on the other side. Thereby, generating the assembly can comprise fixing the grids, scaffold(s) and cleaned downsized tissue together with a ring. The ring can particularly be a ring made of polytetrafluoroethylene (Teflon). Such an assembly comprising the scaffold(s), cells, grid and, eventually, the ring can form a compact assembly which allows a comparably easy static loading or handling, e.g. in connection with the bioreactor.

Preferably, generating the assembly comprises placing the downsized tissue between two scaffolds such that the assembly is a sandwich assembly. Also, the assembly can comprise plural scaffolds alternating with plural layers of downsized tissue. E.g., two layers of cells can alternate with three scaffolds or three layers of cells can alternate with four scaffolds. In cases where a grid is used for generating the assembly, the grid can be arranged on one of the scaffolds and a further grid on the other one of the scaffolds. In particular, the grid can be arranged on the side of the scaffold facing away from the cleaned downsized tissue and the further grid on the side of the other one of the scaffolds facing away from the cleaned downsized tissue.

Preferably, inside the 3D perfusion system the assembly is directly perfused. In this context, the term "direct" relates to perfusing the tissue with a medium through the assembly or construct. In contrast therefore are overflow technologies using microchannels or similar technologies where a 2D-cell layer is supplied with nutrients by continuous flow over and not through the cells. However, it has turned out to be more efficient and to allow growing cells more homogeneously when the cells are directly and three-dimensionally perfused.

Preferably, perfusing the assembly inside the bioreactor is applied in alternate directions. Compared to unidirectional perfusion a perfusion from alternate directions can increase the efficiency of tissue growth.

A further aspect of the invention relates to a method of testing efficacy of tumor or cancer treatment, comprising: obtaining tissue from the tumor or cancer of a patient; culturing the tissue in a method according to any one of the preceding claims; applying a treatment to the tissue; monitoring the tissue; and evaluating changes in the monitored growth, viability and/or volume of the tissue upon treatment.

Thereby, the treatment can comprise provision of one or plural substances or medicaments, application of a particular dosage regimen, irradiation, chemotherapies, irradiation protocols and or any other treatment suitable for treating tumor or cancer patients or combinations thereof. Such a method allows for assessing a particular treatment in regard to its efficiency in a particular or specific tumor or cancer. This makes an efficient evaluation of an appropriate treatment for a particular tumor or cancer possible.

Preferably, this method further comprises: obtaining further tissue from the tumor or cancer of the patient; culturing the further tissue in the method according to any one of the preceding claims; applying a second treatment to the further tissue; monitoring of the further tissue; and selecting the first treatment or the second treatment by evaluating the monitored growth, viability and/or volume of the tissue and of the further tissue upon treatment.

The treatment and second treatment can be performed sequentially or simultaneously. They can be performed for an identical predefined time period. Thereby, the time period can be predefined to a couple of days.

By comparing the in vitro situation of a particular patient-derived tumor tissue sample treated differentially, an appropriate or optimized in vivo treatment can be chosen. This allows for efficiently choosing a preferred treatment for the patient.

Preferably, the first treatment comprises provision of a first substance to the tissue and the second treatment comprises provision of a second substance to the further tissue. The first and second substances can comprise the same or different active pharmaceutical ingredients. The first and second substances can be medicaments suitable for treating tumor or cancer patients.

Preferably, the first treatment comprises a first dosage regimen and the second treatment comprises a second dosage regimen. In such a way the first and second treatments can, e.g., be the provision of one or plural substances at the different dosages.

Another further aspect of the invention relates to a method of enriching cells of a specific cell type from human or animal tumor tissue comprising culturing the tumor tissue in a method of in vitro culturing or expanding human or animal tissue described above for a predefined time period. For example, such cells can be tumor stroma cells, tumor immune infiltrating cells or tumor epithelial cells. Thereby, the method preferably further comprises isolating the cells of the cell type from the tumor tissue.

Preferably, the method further comprises the steps of: comparing plural perfusion media with regard to their capacities of propagating the cells of the cell type; identifying a perfusion medium from the plural perfusion media in consideration of their capacities; and selecting the preferred perfusion medium for perfusing the sandwich assembly in the bioreactor. This allows for efficiently enriching a specific cell type. For enriching tumor stromal cells e.g. RPM11640 can be the preferred perfusion medium. In such a preferred embodiment the tumor tissue can also be cultured in another method than the method of in vitro culturing or expanding human or animal tissue described above.

These and other aspects of the invention will be apparent from and elucidated with reference to the embodiment(s) described hereinafter.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The methods according to the invention are described in more detail hereinbelow by way of exemplary embodiments and with reference to the attached drawings, in which:

FIGS. 2 to 7 show a first specific example of a further embodiment of the method of in vitro culturing or expanding human or animal tissue according to the invention, wherein FIG. 2 shows a primary perfusion culture of CRC specimens;

FIG. 3 shows a tissue forming capacity under perfusion culture;

FIG. 4 shows immunofluorescence stainings for epithelial, stromal and proliferation markers;

FIG. 5 shows an effect of flow on tissue growth;

FIG. 6 shows expansion of tissue over 20 days culture;

FIG. 7 shows survival of cells under suspension;

FIGS. 8 to 14 show a second specific example of a further embodiment of the method of in vitro culturing or expanding human or animal tissue according to the invention, wherein FIG. 8 shows the experimental design;

FIG. 9 shows a representative histological analysis of downsized tumor tissue, i.e. tumor specimen P262: day 0—Original tissue; day 10—After U-CUP culture; Xenograft Day 61—digested tumor single cell suspension injected subcutaneously in immunodeficient mouse;

FIG. 10 shows markers of hematopoietic cells;

FIG. 11 shows a quantification analysis;

FIG. 12 shows Luminal A breast cancer tissue histologies, i.e. in the left panel: original tissue and in the right panel: 3D perfusion bioreactor cultured tumor tissue (H&E: hematoxylin-eosin, CK22: Pan Cytokeratin, ER: Estrogen Receptor);

FIG. 13 shows in-vitro drug test using Luminal A breast cancer

FIG. 14 shows immunohistochemistry of Luminal A Breast Cancer (MAM18) treated for 7 days with PHA (1 ng/mL) in which CD45 stain for total infiltrating lymphocytes, CD3 stains for T-cells, CD68 stains for macrophages.

DESCRIPTION OF EMBODIMENTS

Figure 1:
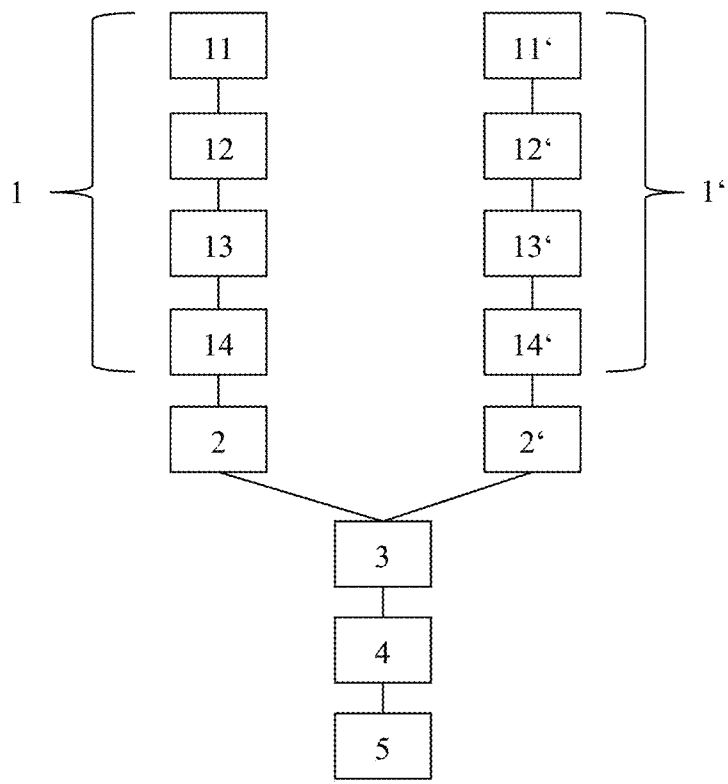
FIG. 1 shows block diagram of an embodiment of a method of testing efficacy of tumor or cancer treatment according to the invention using an embodiment of a method of in vitro culturing or expanding human or animal tissue according to the invention.

FIG. 1 shows an embodiment of the method of testing efficacy of tumor or cancer treatment according to the invention (the selection method) in which an embodiment of a method of in vitro culturing or expanding human or animal tissue according to the invention (the culturing method) is applied. The selection method comprises a first step in which tissue of a tumor and further tissue of the same tumor are identically cultured with the culturing method 1, 1'. Therein, the tissue and further tissue are cleaned by washing and anti-septic treatment and downsized or pre-digested by mechanical and enzymatic treatment 11, 11'. Each of the pre-digested tissue and pre-digested further tissue are arranged in between two disc shaped collagen scaffolds. Grids are arranged on top and on bottom of the scaffold tissue assembly and the scaffold further tissue assembly, respectively. The grid, scaffolds and tissue assembly as well as the grid, scaffolds and further tissue assembly are then fixed together by a polytetrafluoroethylene (Teflon) ring. Thereby, a sandwich assembly and a further sandwich assembly are formed 12, 12'.

The sandwich assembly and the further sandwich assembly are then arranged in culture chambers of 3D perfusion bioreactors as described in 2013/182574 A1 13, 13'. Inside the 3D perfusion bioreactors the sandwich assembly and the further sandwich assembly are then perfused with an appropriate medium for a number of days such as, e.g., for ten days or twenty days 14, 14'.

In a second step of the selection method, a first treatment is applied to the tissue 2 and a second treatment is applied to the further tissue 2'. Thereby, a first medicament for treating tumors is provided to the tissue at a first dosage regimen and a second medicament different from the first medicament is provided to the further tissue at a second dosage regimen. In other embodiments, the first and second medicaments can be the same and the first and second treatments only vary in the dosage regimen applied or the first and second dosage regimen are the same and the first and second treatments only vary in the medicaments used. In other further embodiments more than two treatments are applied to tissue of the tumor.

At the end of the second step the tissue and further tissue are evaluated wherein the efficiency of the first and second treatment are rated 3. For example, comparing the tissue and further tissue, e.g. with regard to volume and/or apoptosis, may lead to a conclusion that either the first or second treatment more efficiently impedes the specific tumor tissue. The more efficient treatment is then selected 4 and applied to the patient 5.

In the following a first specific example of a further embodiment of the method of in vitro culturing or expanding human or animal tissue according to the invention is described in more detail.

Medium, Supplements and Scaffold

Tumor tissue cell specimens are maintained up to 20 days in RPMI (SIGMA-Aldrich®) or DMEM/F12 (Gibco®) containing 1% GlutaMAXTM-I 100× (Gibco®), 1% Kanamycin sulphate 100× (Gibco®), Metronidazol (250×; 200 mg/ml, Braun), Cefuroxim (250×; 15 mg/ml, Braun), 1% Fungizol (Sigma-Aldrich), 1% HEPES 1 M (Gibco®), N-Acetyl-Cysteine 1 mM (NAC, 500×, stock 500 mM, Sigma-Aldrich), Nicotinamid 10 mM (Nic, 100×, stock 1M, Sigma-Aldrich). Additional supplements are Prostaglandin E 2 0.1 ug/ml (Tocris Bioscience) and Epidermal Growth Factor 25 ng/ml (Stem Cell Technologies, Grenoble, France).

For blood-derived culture conditions either patient derived plasma, pooled human serum (Blood Bank, University Hospital Basel, Switzerland) or fetal calf serum (Gibco®) in a 10% concentration is used. For serum-free culture standard organoid culture supplements B27 2% (Invitrogen) and N2 1% (Invitrogen) were used.

Collagen (UF) Scaffolds (Ultrafoam Avitene Collagen Hemostat®, UF) are obtained from Davol Inc., Warwick, USA. A non-woven polyethylene (185 g/m2, needlepunch, cat. N. 72.185.503, PET) scaffold mesh is obtained from Norafin Industries, Mildenau, Germany. Collagen-cross-linked scaffolds (Optimaix) are obtained from Matricel GmbH, Germany. The scaffolds are cut by a biopsy punch for 8 mm for the collagen-sandwich-assembly.

Human Tissue Materials

Fresh surgically resected colorectal cancer (n=24), glioblastoma (n=3) or breast cancer specimen's (n=11) samples are obtained from patients operated at the University Hospital Basel, Regional Hospital Olten or regional Hospital Lugano. Initial tissue samples are 3-5 mm in diameter and excised by a pathologist from the tumor center. The tissue is carefully washed in 4° C. phosphate buffered saline (PBS, Sigma-Aldrich).

Preparation of Minced and Chunked Tissues or Downsized Tissue

The tissue is washed three times with PBS and minced in pieces with a scalpel. Minced tissue is then enzymatically pre-digested in DMEM (GIBCO) with collagenase IV (100×, stock 20 kU/ml, Worthington CLSS-4), DNAse I (100×, stock 50 mg/ml, Sigma-Aldrich D5025), HEPES (100×, stock 1M, GIBCO 15630-056), Kanamycin (100×, GIBCO 15160-047), Amphotericin B (100×, stock 250 ug/ml, Sigma-Aldrich A9528), Metronidazol (250×; stock 200 mg/ml, Braun), Cefuroxim (250×; stock 15 mg/ml, Braun) for 1 hour at 37° at continuously smooth rotation on a MACSmix tube rotator (Miltenyi Biotec). The generated chunk tissue is washed once with PBS including EDTA 1:250 & 10% pooled Human Serum (Blood Bank, University Hospital Basel, Switzerland), and treated afterwards for 5 min with a 2.5% Octenisept (Schülke&Mayr, Germany)- 10% Human Serum-PBS solution. To remove the Octenisept completely an additional wash with EDTA-HS-PBS is performed.

3D Perfused Culture in Collagen-Sandwich Assembly

To culture tissue chunks in 3D under perfusion the perfusion bioreactor system for cell seeding and culture of 3D scaffolds described in WO 2013/182574 A1 are used. The pre-digested tissue fragments (chunks) are therefore placed on the scaffold together with the remaining cell digest. 2-3 larger tissue fragments (0.5 mm in size) could be placed. Scaffolds are then transferred to the scaffold holder and another scaffold is applied to obtain the collagen-sandwich assembly. A grid is used on top and bottom of the collagen-scaffold and the scaffolds held fixed by a Teflon ring. This construct is then placed in the culture chamber of the perfusion bioreactor. A flow rate of 0.3 ml/min is chosen for perfusion culture.

Medium change is performed twice a week. Constructs are harvested at either 10 or 20 days. DNA quantification, histological and immunofluorescence analysis are performed for those time points.

Organoid Cell Culture of Chunked Tissues

For organoid cell culture of chunk tissues a previous method previously described by Sato et al. (Gastroenterology 2011) is used. Briefly fragments, measuring 0.5-1 mm, were cultured on coated Matrigel (growth-factor reduced, phenol red free, BD Bioscience, Switzerland) 24-well plates. Culture medium with supplements is overlaid and tissue fragments cultured for the same culture period as 3D perfused cultures.

DNA Quantification

Collected samples as described hereinbefore are further digested with proteinase K solution (1 mg/ml proteinase K, 50 mm TRIS, 1 mm EDTA, 1 mm iodoacetamide, and 10 µg/ml pepstatin-A; Sigma-Aldrich, USA) in double distilled water or potassium phosphate buffer for 16 h at 56° C. as previously described.

DNA quantification is performed by means of a commercially available fluorescence based kit, namely CyQUANT® Cell Proliferation Assay (Invitrogen, USA). Working solutions were prepared according to the manufacturers protocols. The analyses are carried out measuring fluorescence with a Spectra Max Gemini XS Microplate Spectrofluorometer (Molecular Devices, USA). Excitation and emission wavelengths are 485 nm and 538 nm, respectively. Samples in each plate include a calibration curve. Each sample was measured in triplicate.

Histological Staining and Immunofluorescence

Tumor-Collagen tissues after 3D perfusion culture are fixed overnight in 1.5% paraformaldehyde at 4° C., paraffin embedded (TPC15 Medite, Switzerland) and sectioned (5 m-thick) by means of a microtome (Leica, Switzerland). Paraffin sections are deparaffinized, hydrated and stained with hematoxylin and eosin (H&E), followed by observation under light microscopy.

Immunofluorescence analyses on paraffin embedded sections are performed after antigen retrieval at 95° for 30 min with target retrieval solution ready-to-use (DAKO, S1700). To characterize the proliferating cell population a Ki67 monoclonal antibody 1:100 (Rb mAb FITC, AbCAM, ab27619) is used. For visualization of stromal cells Vimentin monoclonal antibody (Rabbit mAb, Cell Signaling 5741) and for epithelial cells EPCAM monoclonal antibody (Mouse mAb, Cell Signaling 2929) are applied. To improve the signal strength a secondary monoclonal antibody goat-anti-rabbit, Alexa-Fluor 488 1:400 (IgG, Invitrogen), resp. monoclonal antibody goat-anti-mouse Alexa-Fluor 546

1:400 (IgG, Invitrogen) is applied. Nuclei are stained with DAPI 1:100 (Invitrogen). Histological and immunohistochemical sections are analyzed using a BX-61 microscope (Olympus, Germany).

Flow Cytofluorometric Analysis

Supernatant of cultured primary samples is stained with EPCAM-APC (ab27619, clone SP6, Abcam, Cambridge, UK) and Propidium Iodid (Sigma-Aldrich). Analyses are performed using a FACSCalibur flow cytometer (BD Biosciences, Germany). Gates are adjusted according to isotype control reps. unstained sample.

Statistical Analysis

Statistical Analysis is performed as previously described (Flis et al. Anticancer Res 2009). The data is presented as mean values±standard deviation (SD).

Results

To culture primary colorectal cancer specimens for in-vitro 3D culture advantage of a previously described perfusion bioreactor adapted to specific needs (FIG. 2) is taken. As earlier reports mentioned the critical dependence of primary tumor cells on niche-signals, cellular heterogeneity and 3D architecture, either pre-digested minced tissue or tissue fragments for perfusion culture are used. Enzymatic pre-treatment of tissue fragments enhances their tissue forming capacity (FIG. 2.1), as previously reported.

Commensal microorganisms heavily contaminate CRC tissue specimens. Therefore, an initial wash with PBS-EDTA supplemented with 10% HS and a short treatment with 2.5% Octenisept is performed to reduce bacterial load.

Figure 2:
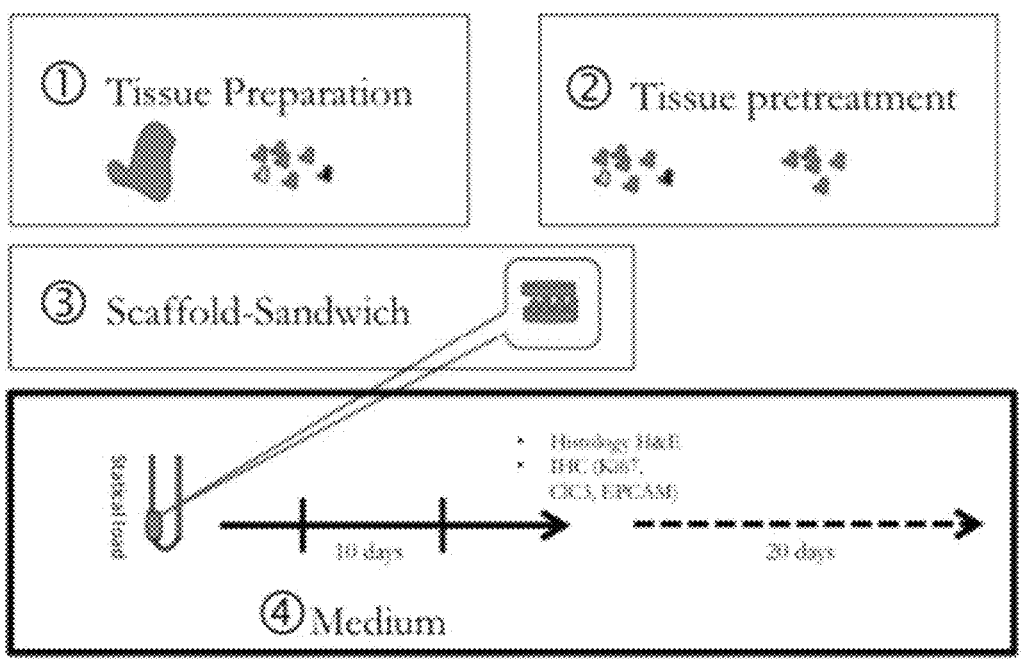
Figure 3:
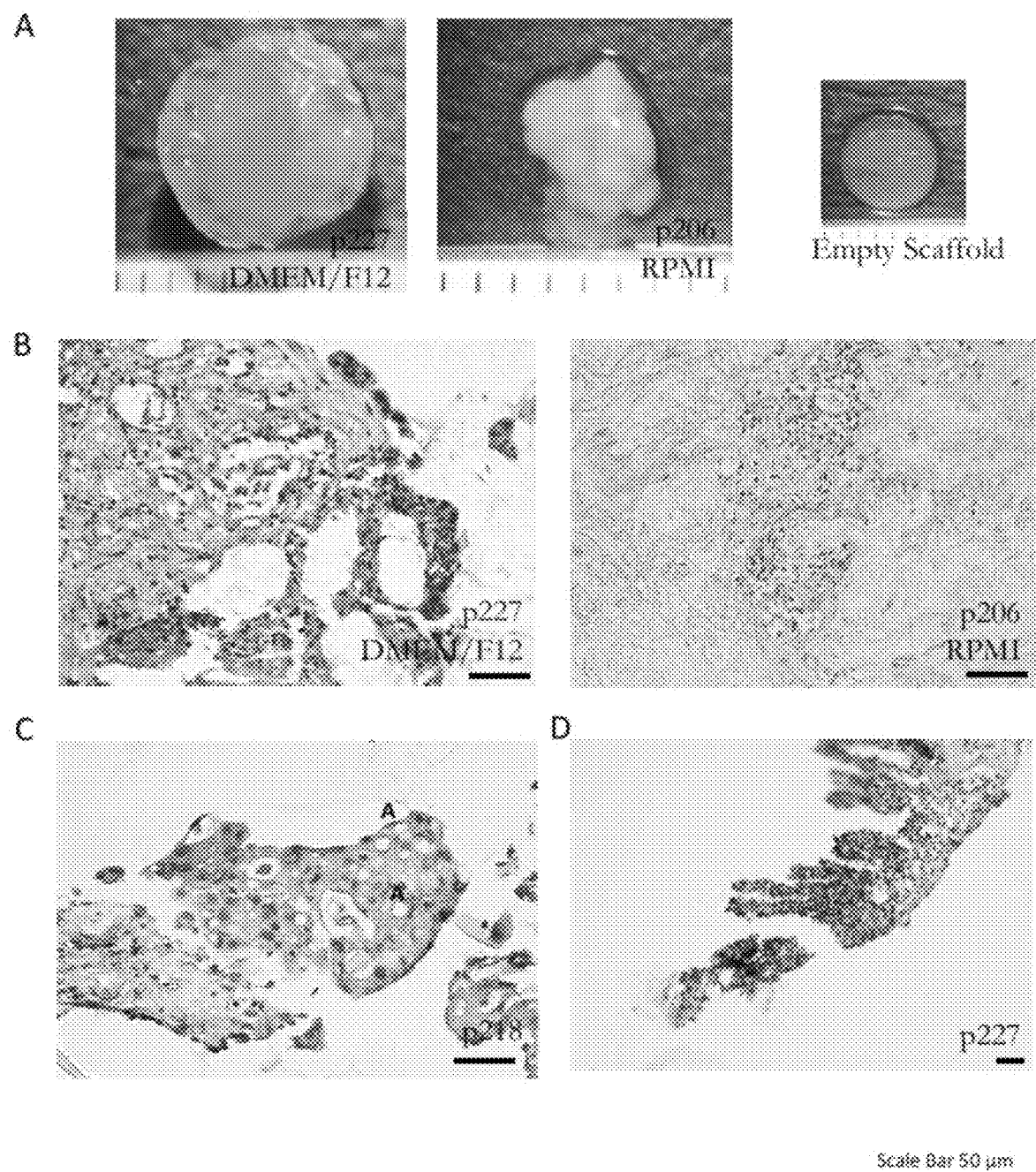

Following preparation and pre-treatment tumor fragments are placed between two collagen scaffolds, e.g. in a "scaffold-sandwich" or sandwich assembly. This step is necessary not only to keep tissue specimens in place after static loading under perfusion but also to allow expansion and remodeling of the tumor in the surrounding scaffold. A ten days perfusion culture results in a profound restructuring of collagen scaffolds as compared to their empty counterparts (FIG. 3). Other scaffolds tested, like polyethylene or crosslinked collagen scaffolds are less suitable for the generation of tissue-like structures (FIG. 2.3).

Initial studies have shown the superiority of autologous human plasma over fetal calf serum with denser and larger tissue formation by H&E stainings. As availability of autologous human plasma is usually limited, pooled human serum for tissue culture is used which could obtain similar tissue structures over time. Pooled human serum shows a trend in superior tissue yield and quality as compared to conventional serum-free approaches using B27/N2 as evaluated by organoid and perfusion cell culture. As described for static 3D cultures addition of Prostaglandin E 2 (PGE2) and epidermal growth factor (EGF) could help to further increase tissue formation. Measured by the total DNA-amount and evaluated histologically, a similar trend is found and therefore used for perfusion culture medium supplemented with commercially available pooled human serum together with EGF and PGE2.

Using the approach described hereinbefore for tumor culture after ten days culture a strong remodeling of collagen scaffolds is observed. Large tumor-nodules ranging up to one millimeter in diameter are clearly visible in all cases tested. The remodeling capacity depended on the individual patient and tissue status, e.g. fresh or frozen, prior to culture. Interestingly, RPMI1640 medium appears to induce a stronger restructuring of the collagen scaffold as compared to DMEM/F12 Medium (FIG. 3.A).

Figure 4:
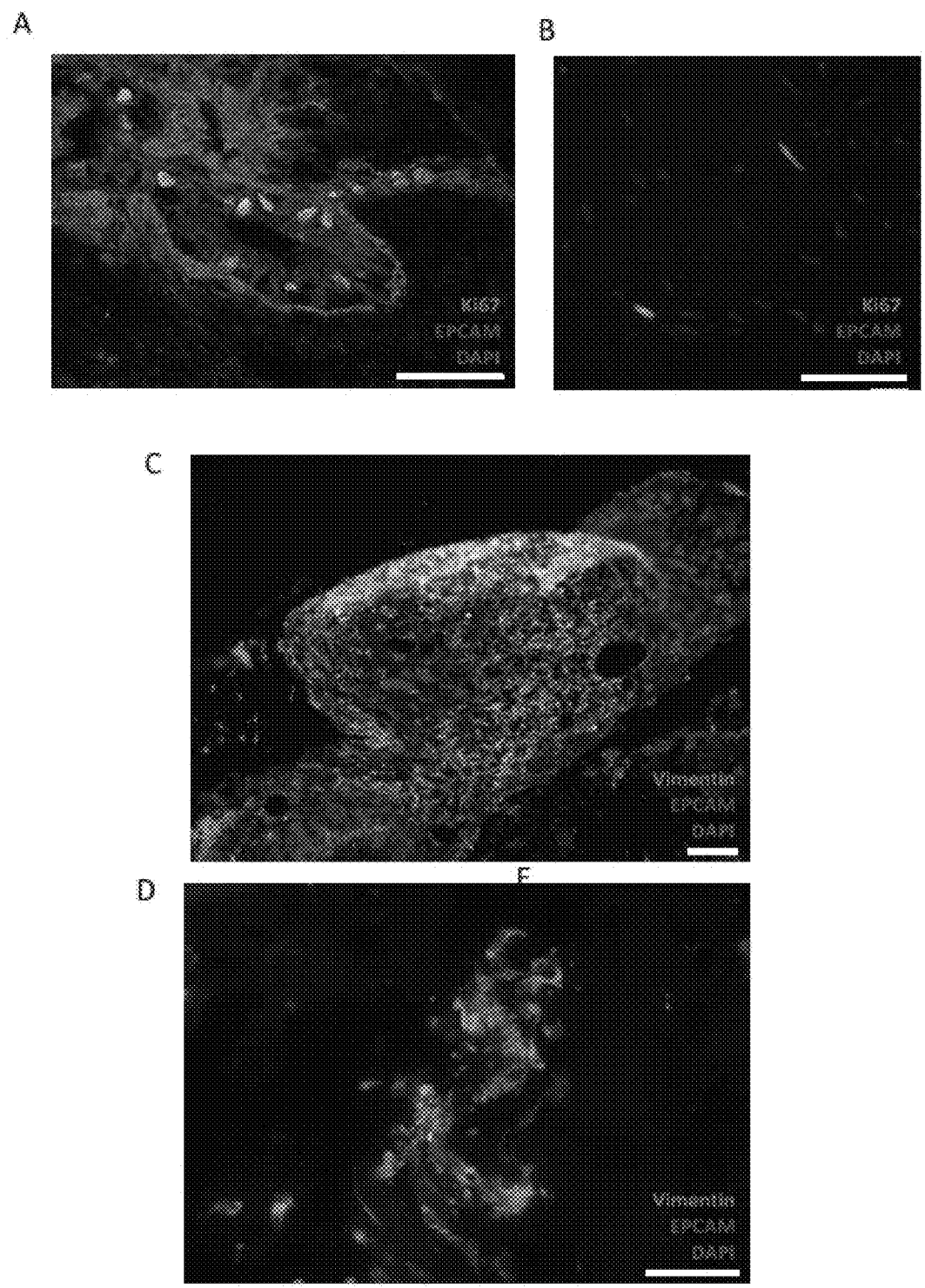

Upon histological evaluation, a heterogeneous tissue formation with both epithelial and stromal parts is observed, as detectable by EPCAM or Vimentin specific staining, respectively (FIGS. 4.B, 3.C). In some cases infiltration by lymphocytes can be observed. RPMI1640 medium promotes stromal proliferation to a slightly higher extent than DMEM, as visible by macroscopic view and histological evaluation (FIG. 3.B). Interestingly, epithelial cells formed barriers or acini structures and eventually lead to maintenance of villi-like protrusions (FIGS. 3.C, 3.D), recapitulating gut morphology. Nevertheless, the epithelial structure still displays a highly dysmorphic and anaplastic phenotype consistent with its origin from the initial tumor mass.

Immunofluorescence evaluation by staining for EPCAM, shows that nodular structures are largely, albeit not exclusively, of epithelial nature. Tissue is viable and proliferating, as stained with the proliferation marker Ki67 (FIG. 4.A). Proliferation could be seen on both stromal and epithelial parts. The frequency of proliferating cells is similar to that observed in the initial tumor specimen.

Figure 5:
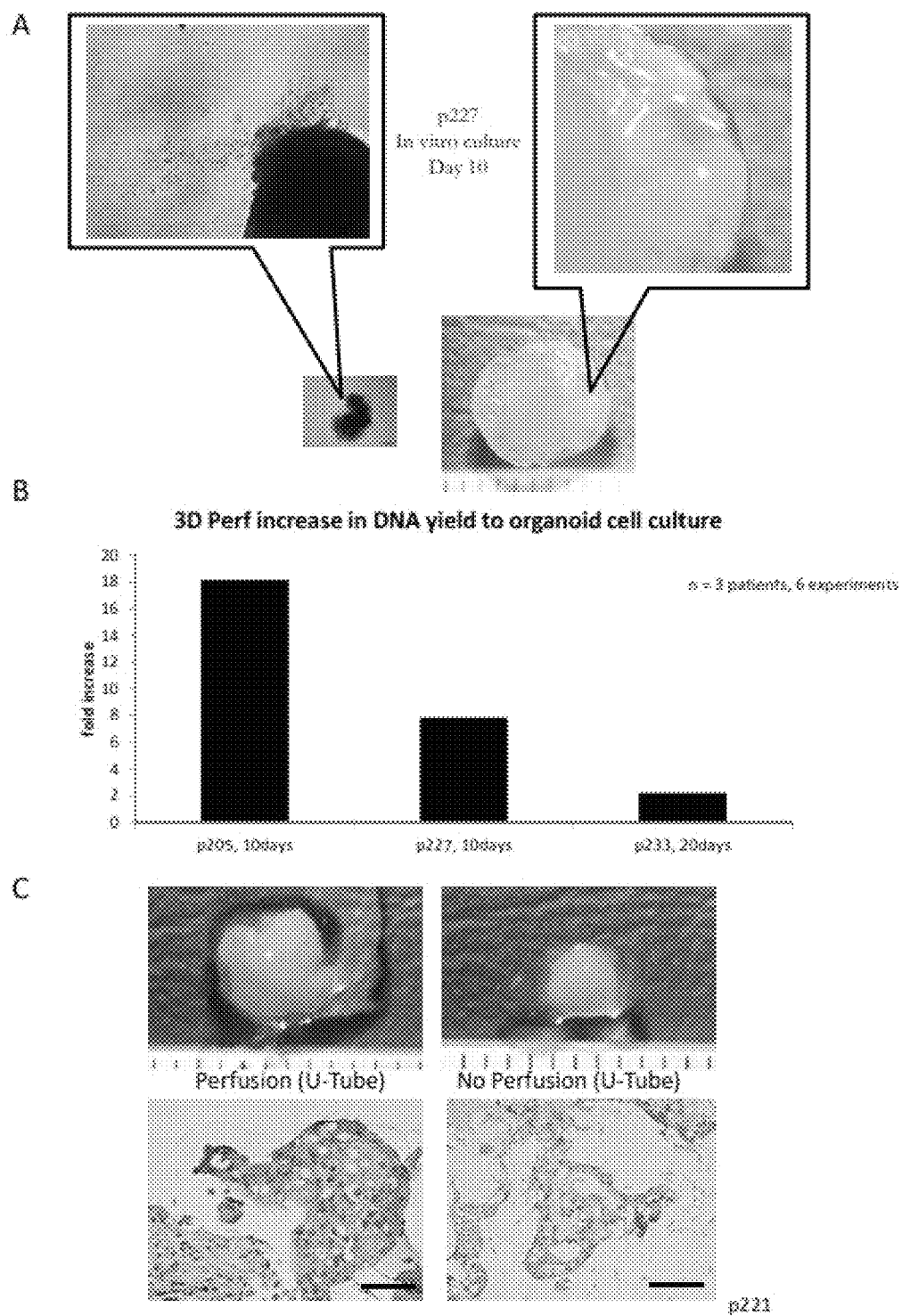

To evaluate the use of perfusion in primary tumor culture, the 3D perfused cultures are compared to the culture of tissue chunks by the organoid culture technique. Macroscopically, as above mentioned, after ten days perfusion culture large tumor nodules are visible measuring up to 2 millimeter, where in organoid static cultures only slight size differences and evasion of single cells can be observed (FIG. 5.A).

Depending on samples after ten days an up to 13 fold increase (+1-7.3) in total DNA-amount is reached in perfused, as compared to static cultures. The difference after twenty days culture is reduced but remained at 2.2 fold (FIG. 5.B). Indeed, if tumor specimens are cultured within the scaffold-sandwich in static conditions, only a small sample is recovered after ten days culture and the surrounding collagen scaffold is mostly digested. In the perfused culture a scaffold remodeling takes place. In addition, in the absence of perfusion tissues are largely degraded and signs of tissue lysis are visible.

Figure 6:
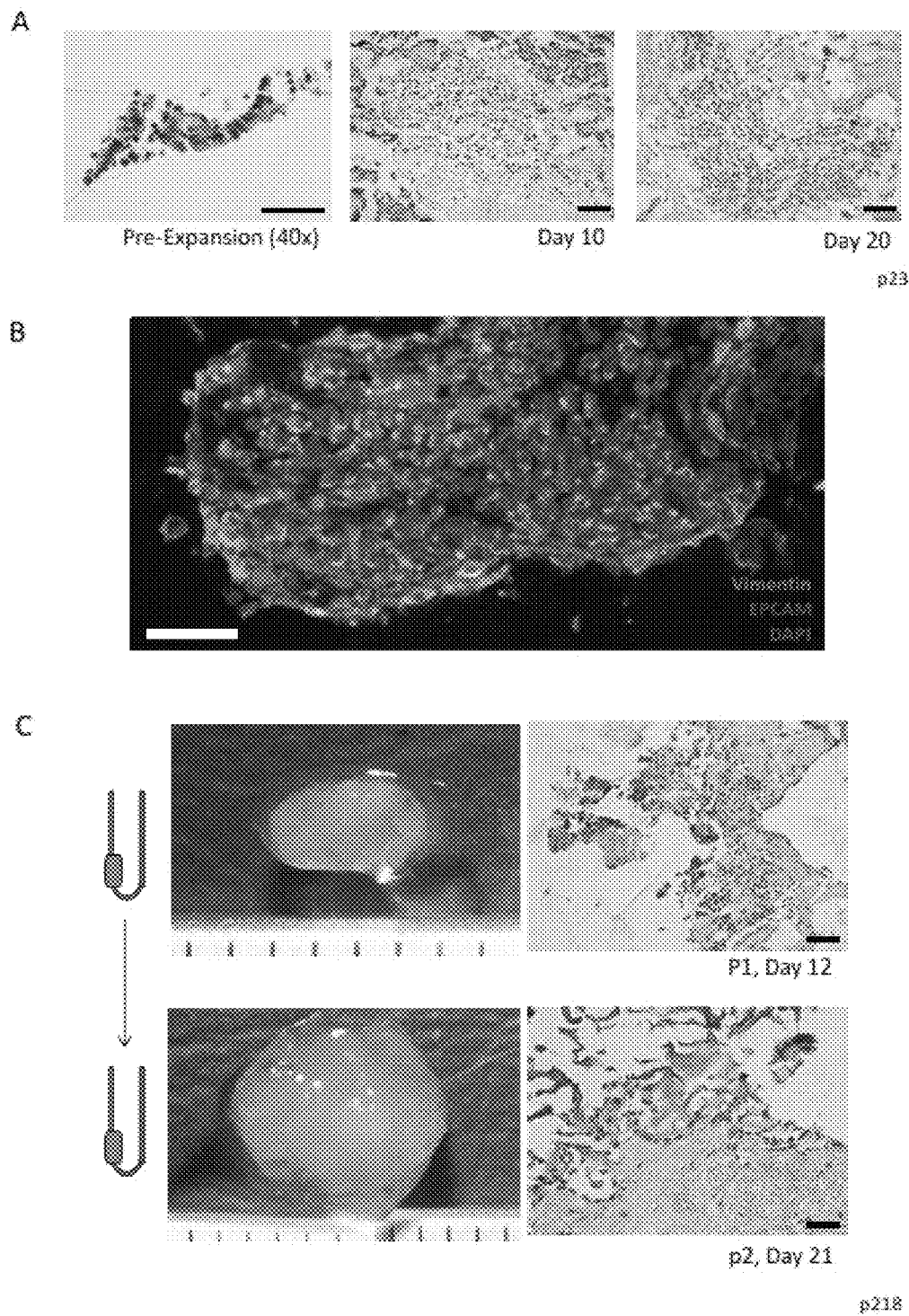

As tumor tissue for ten days under perfusion culture can be kept alive and proliferating, it is evaluated whether tumor tissue can be expanded through longer time. Therefore tumor tissue is cultured either for ten or twenty days and a histological analysis (FIGS. 6.A, 6.B) is performed. Compared to the initial tumor fragment an expansion of the tissue and maturation over time can be observed reaching a compact tissue at day twenty. Both stromal and epithelial cells can be preserved over time.

To assess the potential of the 3D perfused culture technique tumor tissue is cultured for twelve days and half of the tumor-tissue is re-cultured afterwards for additional nine days. The collagen scaffold shows at the first time point several tumor-nodules and at the later one a higher central density with slight remodeling. Histologically epithelial and stromal cells can be observed at both time points integrating in the collagen scaffolds.

Figure 7:
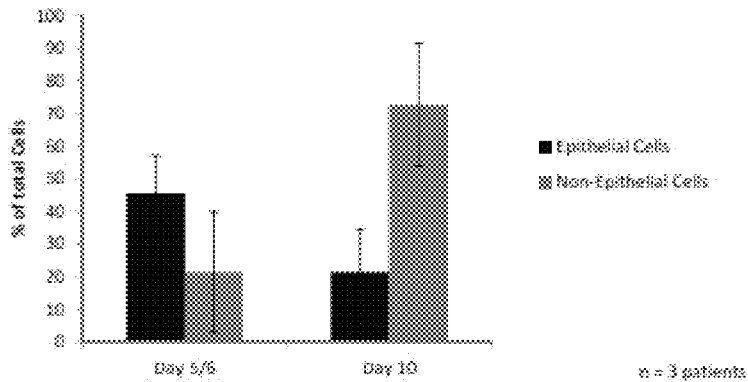
Figure 7:
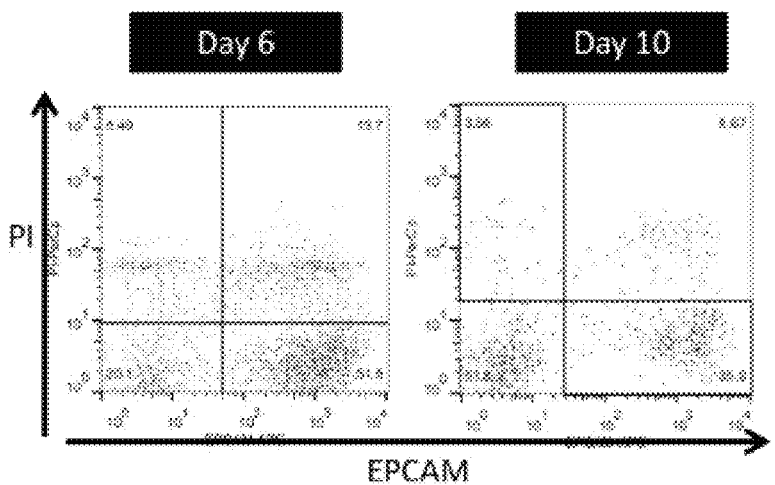

As tumor tissue is shedding cells in the circulation during the growth, tumor cells can be detected as circulating tumor cells in the blood stream. The number of circulating tumor cells is correlating with prognosis and correlating as well with treatment response. Interestingly by FACS analysis of the perfused medium living tumor cells can be detected over time, as evaluated by with EPCAM and PI (FIG. 7). Shed viable tumor cells are detected over twenty days and the percentage varies from tumor. A substantial number of cells are of non-epithelial nature as well.

Discussion of the Above First Example

Primary tumor culture from patient biopsies or surgical specimens in vitro have been a long time goal in science since decades. Despite the significant efforts performed in the past, primary culture remains very difficult to be established. For many types of cancer, it is far easier to grow the normal cells than the cancer cells. Even for cancers that are relatively easy to grow, such as melanomas, only the metastatic cancers can be established as immortal cell lines. Previous studies showed that primary tumors strongly depend on signals from the tumor microenvironment for successful in vitro culture. Preservation of the tumor microenvironment consisting of both benign and malign cells remains even with this organoid cell culture technique difficult to achieve With the methods according to the invention a new protocol can be achieved to prepare and directly culture in vitro fresh colorectal cancer tumor specimens for a high efficient in vitro culture using a perfused bioreactor system. As single cells digest of tumor tissue are in most cases leading to an in vitro cell-death due to missing micro environmental signals, mechanically and enzymatically pre-treated colorectal cancer specimens is used leading to cell clumps and tissue fragments of hundreds of cells. For the first time this helps not only to prevent cell death in vitro but as well keeps the initial heterogeneous tumor microenvironment consisting of epithelial, stromal and immune cells together. Presumably, this mechanical and enzymatic stress leads to the initiation of tissue healing process, which could be of help to in tissue generation in vitro.

Because colorectal specimens are heavily overgrown by commensals a reduction and inhibition of the bacterial growth is in this context essential. Bacterial growth in best conditions, as a perfused 37° mediums offers, exceeds cellular growth several fold. Addition of a cocktail of antibiotics is besides this successful pre-treatment necessary. For other tumors where the interaction with commensals is less pronounced fewer antibiotics can be used, as this additives lead as well to a reduction in proliferative capacity of the cells itself.

Interestingly, the culture with autologous patient derived plasma or pooled human serum is superior to fetal calf serum, where only few fragments of tissue are surviving. Fetal calf serum-sensitized human lymphoid cells are active in cytotoxicity assembly s against a wide variety of cultured human tumor and normal target cells. As in the present conditions lymphoid cells are present, non-specific activation due to FCS can lead to tissue destruction. Serum-based medium is still superior to serum-free approaches. Further additives like EGF or PGE2 can be helpful to increase tissue-regeneration capacity depending on individual tumor properties.

By using direct perfusion of tumor-constructs in a collagen-sandwich assembly not only a survival of the heterogeneous tumor tissue can be observed but as well a strong remodeling and integration into the scaffold. For general tissue engineering purposes scaffolds are besides cells and growth factors one of the main important parts and are crucial to build up a physiological architecture. Collagen scaffolds have a high compatibility for supporting growth of different cell types and have been shown to enhance the histogenesis under perfusion in bioreactor systems.

Compared to the established organoid cell culture where epithelial cells are selected during the culture phase stromal survival for twenty days and longer can be observed in the perfused bioreactor. This is important in the context, that tumor-stromal interactions are crucial in modifying drug responses. Without flow, tissue degraded in static conditions possible due to limitations in oxygen and nutrient availability. A flow culture of tumor tissue can lead to a several fold higher tissue amount in regard to static assemblies. Flow is able to mimic to some extend vascularity resp. the natural occurring interstitial flow with additional mechanically stimulation of the cells through shear stress.

Tissue formation under perfusion is possible in 66% of all cases and even higher if contaminated samples are excluded as commensals are a major problem for colorectal cancer in vitro culture. This exceeds significantly the reported 30% efficiency for primary colorectal cancer organoid culture and places it similar to patient derived xenograft (PDX) with reported efficiency for successful tumor generation of 60% to 70%. As for PDX-models up to two months are necessary to grow a 6-8 mm measuring tumor (own experience), perfusion culture in bioreactor is able to integrate tumor tissue in scaffold in much shorter time.

The tissue quality and composition is varying from patient to patient and there is some heterogeneity from culture to culture even coming from the same patients, as the starting tissue was not homogenous. Proper selection of initial tissue specimens is important to obtain successful cultures. The standardization is a major limitation of general tissue resp. organoid-like cultures and future studies are necessary to reduce the heterogeneity in tissue-forming capacity from same starting material. Stringent selection criteria for tissue prior culture (size, form, pathological assessment) or increase in parallel bioreactor culture can be used to circumvent this issue—nevertheless starting material is generally limited.

The culture techniques described hereinbefore can also be used for other tumor types like breast-cancer, melanoma, bladder-cancer, prostate-cancer, glioblastoma and any other tumor tissue.

In the perfused 3D culture described hereinbefore the tumor microenvironment is preserved over time, therefore drug testing in individualized manner can be possible. This opens new fields in personalized drug screening. One of the major limitations is still the amount of tumor material available. Since, as can be seen in Table 1 below, also tumor tissue growth from frozen tissue specimens can be achieved, screening can be done in centers and tumor tissue transported in freezing medium. In this context, markers for treatment response should be identified and implemented for such screenings. By using colorectal cancer cell lines, it is found that anti-apoptotic genes like c-Flip, Traf-1 and Bcl-2 can be markers for treatment response similar to neoadjuvant treated rectal cancer patient samples.

TABLE 1

Test results for fresh and frozen tissue

| Nr | Patient | Tissue Type | Tissue Prep | Medium | Suppl. | Scaffold | Culture Time | Outcome |
|---|---|---|---|---|---|---|---|---|
| 1 | P191 | Fresh | Chunk | RPMI | aHP/FCS | UF | 10 | Tissue |
| 2 | P192 | Fresh | Chunk | RPMI | aHP/FCS | UF | 10 | No tissue |

TABLE 1-continued

Test results for fresh and frozen tissue

| Nr | Patient | Tissue Type | Tissue Prep | Medium | Suppl. | Scaffold | Culture Time | Outcome |
|---|---|---|---|---|---|---|---|---|
| 3 | P193 | Fresh | Chunk | RPMI | aHP/FCS | UF | 10 | Tissue |
| 4 | P202 | Fresh | Chunk/Mince | RPMI | aHP/HS | UF | 10 | Infection |
| 5 | P205 | Fresh/Frozen | Chunk | RPMI/DMEM | aHP/HS | UF | 10 | Tissue |
| 6 | P206 | Fresh | Chunk | RPMI | aHP/HS | UF | 10 | Tissue |
| 7 | P207 | Fresh | Chunk/Mince | RPMI | HS | UF | 10 | Infection |
| 8 | P208 | Fresh | Chunk/Mince | RPMI | HS | UF | 10 | Tissue |
| 9 | P217 | Fresh | Chunk | RPMI | HS | UF | 7 (–34) | Tissue |
| 10 | P218 | Fresh | Chunk | RPMI | HS | UF | 12-21 | Tissue |
| 11 | P220 | Fresh | Chunk | RPMI | HS | UF | 6-16 | No tissue |
| 12 | P221 | Fresh | Chunk | RPMI | HS | UF | 9 | Tissue |
| 13 | P227 | Fresh | Chunk | DMEM | HS/B12 | UF/PET | 10 | Tissue |
| 14 | P233 | Fresh | Chunk | DMEM | HS/B12 | UF | 10-20 | Tissue |
| 15 | P234 | Fresh/Frozen | Chunk | DMEM | HS/B12 | UF | 3-12 | Infection |
| 16 | P259 | Fresh | Chunk | DMEM | HS | UF | 10 | Tissue |
| 17 | P261 | Fresh | Chunk | DMEM | HS | UF | 10 | Infection |
| 18 | P262 | Fresh | Chunk | DMEM | HS | UF | 10 | Tissue |
| 19 | P263 | Fresh | Chunk | DMEM | HS | UF | 10 | No tissue |
| 20 | P266 | Fresh | Chunk | DMEM | HS | UF | 10 | Tissue |
| 21 | P268 | Fresh | Chunk | DMEM | HS | UF | 10 | Tissue |
| 22 | P271 | Fresh | Chunk | DMEM | HS | UF | 10 | Infection |
| 23 | P272 | Fresh | Chunk | DMEM | HS | UF | 10 | Tissue |
| 24 | P273 | Fresh | Chunk | DMEM | HS | UF | 10 | Tissue |
| 24 | P276 | Fresh | Chunk | DMEM | HS | UF | 3-7-10 | Tissue |

Culturing of the whole tumor microenvironment in vitro can help further to better understand effects of it on the tumor growth. This can open the screening of drug-ability of new targets, which are difficult to assess by using tumor cell lines alone. New physiological phenotypic screenings integrating the complex microenvironment are in context of tumor research of great potential.

Additionally, tumor infiltrating lymphocytes (TIL) in the tumor microenvironment contribute significantly to survival of patients. Expansion of this population and re-transfusion during adoptive cellular therapy is highly efficient. Systems to expand specifically TIL population and/or methods to select for tumor specificity can be of great value in this context. The technique for primary tumor culture described hereinbefore can be of importance in this regard.

In the following a second specific example of a further embodiment of the method of in vitro culturing or expanding human or animal tissue according to the invention is described in more detail.

Figure 8:
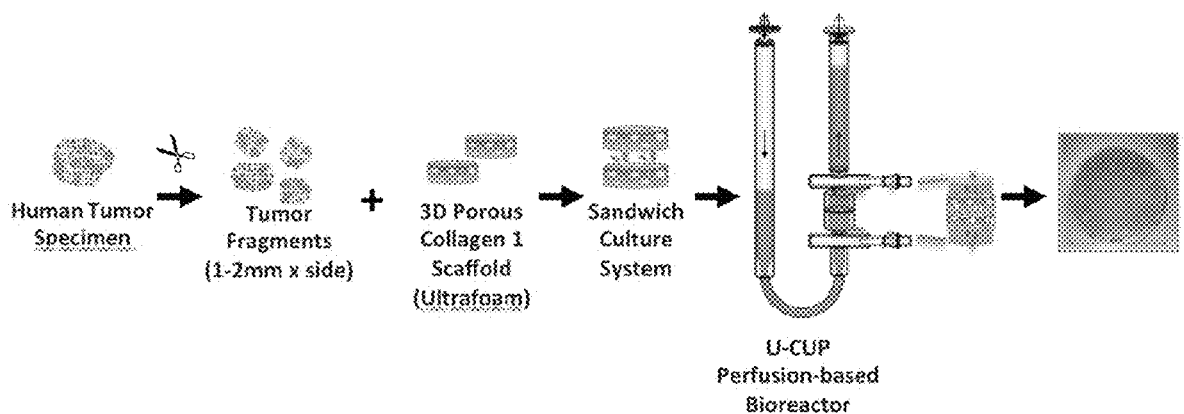

As shown in FIG. 8, in the second example a 3D perfusion bioreactor as described in WO 2013/182574 A1 is adapted for the culture of pieces of human primary tissues. The system is tested mainly for colorectal cancer and Luminal A breast cancer. Thereby a tissue specimen is manually cut in small chunks at a size of 1 mm to 2 mm per side. The pieces are placed in between two collagen scaffolds having a diameter of 8 mm to create an assembly or "sandwich" that it is then placed in a perfusion chamber of the 3D perfusion bioreactor. For each bioreactor, 8-10 mL of culture media are used. The chunks are cultured for 10 to 20 days without medium change.

To increase the standardization the specimen can also be cut using a tissue chopper device (McIlwain Tissue Chopper; Ted Pella Inc.). However, the possibility to use such an instrument depends on the mechanical properties of the tissue (soft or hard) that is tumor-type and patient dependent. The choice not to perform medium change is for limit availability of autologous serum. Anyway, due to the low amount of cells and the low rate of proliferation the consumption of the medium is also slow that realistically allowed to avoid the medium change. A pH evaluation shows that there was no variation overtime. Autologous serum (AS) can be prepared by collecting a total blood sample from the tumor tissue related patient with a syringe without addition of anticoagulants; centrifuging the blood at 2600 g for 30 minutes and at 4° C.; and collecting the supernatant defined as AS. Autologous plasma (aHP) can be obtained by the same procedure but collecting blood using anticoagulants (like Heparin or EDTA).

For culturing in the 3D perfusion bioreactor the tumor tissue is prepared. Due to its own origin, colorectal cancer tissue is highly subjected to risk of contamination, and require a step of cleaning. As soon as the tissue arrives from the pathology, the tissue follows this procedure: (i) Washing in PBS for 3 times, (ii) antiseptic treatment: 10 minutes in 10% Octenisept solution, and (iii) washing in phosphate buffered saline (PBS).

The scaffold or assembly is also prepared within the second example. The sandwich culture system requires two scaffolds to hold the tumor chunks in the perfusion chamber of the 3D perfusion bioreactor. The scaffold provides a mechanical and a biological support to the tumor chunks. The material of choice is collagen type 1 (Avitene Ultrafoam, ref #1050050). This material arrives as a dry sponge and requires a pre-wetting step that determines its shrinkage of 20% in length. A pre-wetting step is made at 4° C. overnight or at 37° C. for 2-3 hours. As wetting solution, PBS or the culture medium could be used. Moreover, during this step, the scaffold can be coated with other material to increase its mechanical and/or biological properties such as, for example, using a solution of Matrigel as coating.

The medium used for tumor chunks culture is a modified version that supports the use of autologous serum. It is composed as follows: DMEM/F12 (Invitrogen, 11320-074), supplemented with: Human Serum 10% or Autologous Serum 10%, Glutamax (Gibco, 35050-061, 100×), Hepes (Gibco, 15630-056, 100×), Kanamycin (Gibco, 25389-940, 100×), and a cocktail of Antibiotics (only for colorectal cancer) comprising of: Ciproxine (Bayer, 200×), Metronidazole (Braun, 200 mg/ml, 250×), Cefuroxime (Braun, 15 mg/ml, 250×), Anfotericin B (Sigma-Aldrich, 100×), N-Acetyl-L-Cysteine (Sigma-Aldrich, A9165-5G, 1 mM), Nicotinamide (Sigma-Aldrich; N0636), Epidermal Growth Factor (EGF, Peprotech, 25 ng/mL), and Prostaglandin E2 (PGE2, 1 ng/mL).

Figure 9:
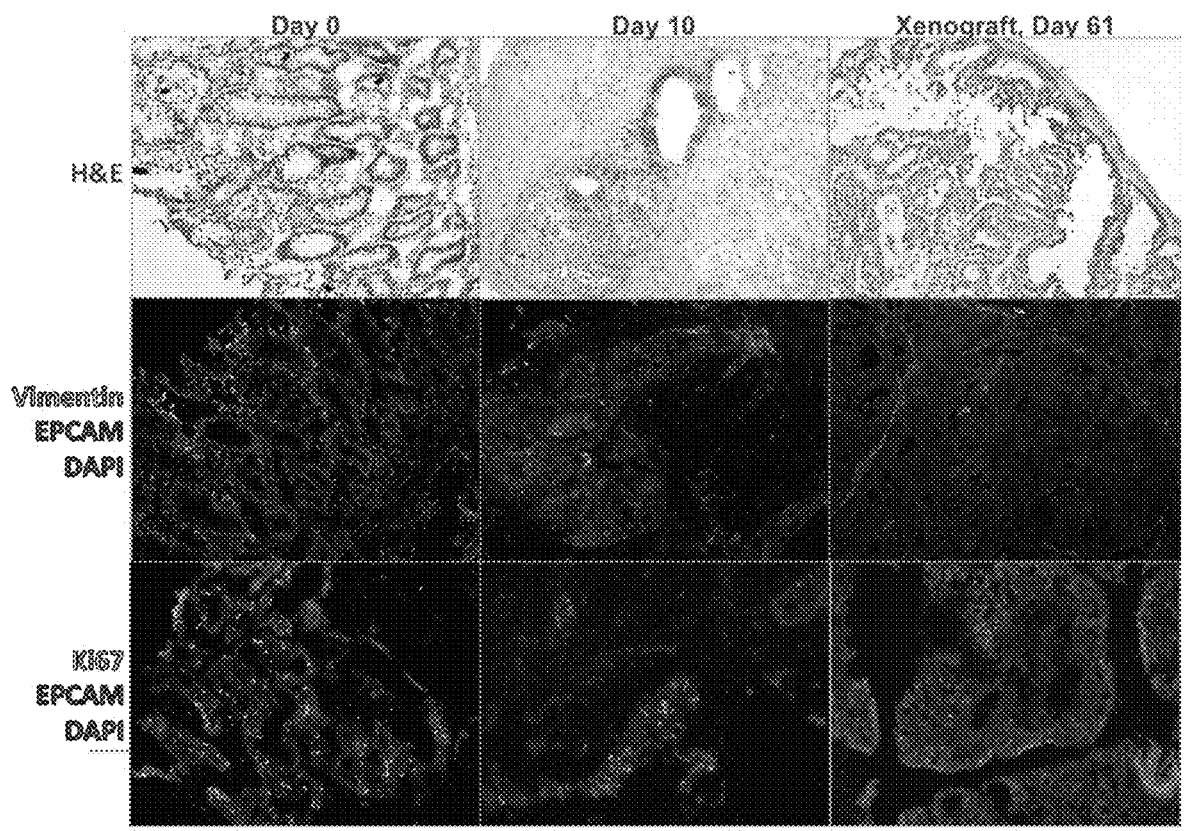

FIG. 9 shows the results of the second example for human colorectal cancer. In particular, it presents the results of a representative experiment. It is reported the original material from the patient, the tissue after 10 days of culture in the 3D perfusion bioreactor, and the tissue obtained after injection of digested-tissue as single cell suspension in immunodeficient mouse, generating after 61 days a patient derived xenograft (PDX). The hematoxilin-eosin staining (H&E) showed the maintenance of tissue organization in the 3D perfusion bioreactor culture, even if at lower grade compare to PDX. Most importantly it is the preservation of epithelial tumor cells (EpCAM positive) and stromal cells (Vimentin positive) in an in-vitro culture system. To notice, after 10 days of culture several cells, mainly EpCAM positive, are showing sign of proliferation by the expression of Ki67 protein, even if at lower extent compare to the original tissue.

Figure 10:
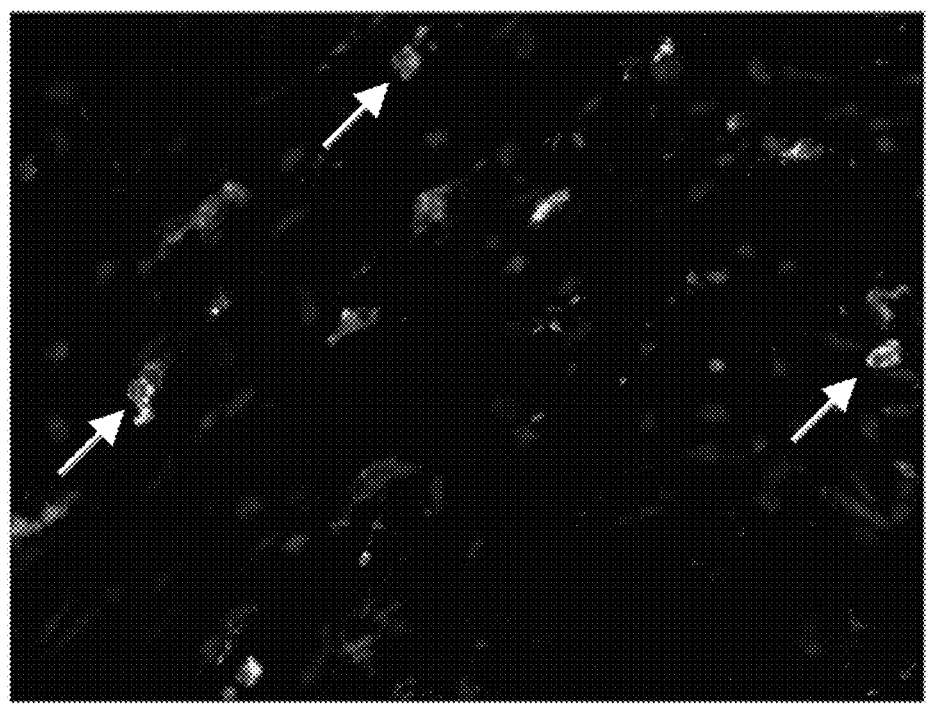

FIG. 10 shows a positive staining for CD45, marker of hematopoietic cells except erythrocytes and platelets, that is used to identify all tumor infiltrating lymphocytes (TIL), which shows that after 10 days of culture these type of cells are still present. However, their functionality is to be assessed.

Figure 11:
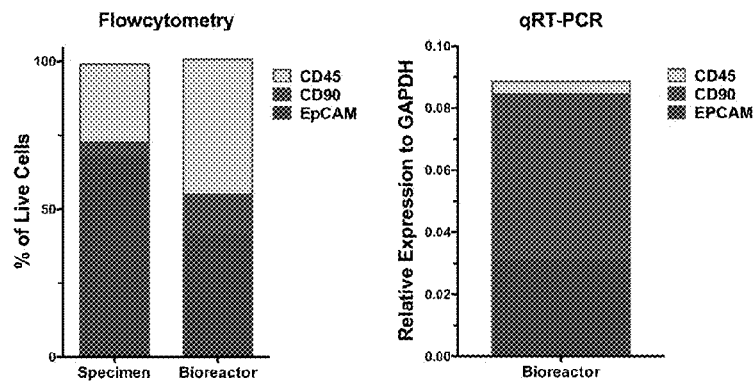

As shown in FIG. 11 a quantification analysis, showing the presence of all main tumor cellular components, can be performed by flow cytometry or even by qRT-PCR. A full comparison with the original tissue, that can show the possibility to maintain the similar proportion among the different cell types, could also be performed (FIG. 11 Flowcytometry).

Figure 12:
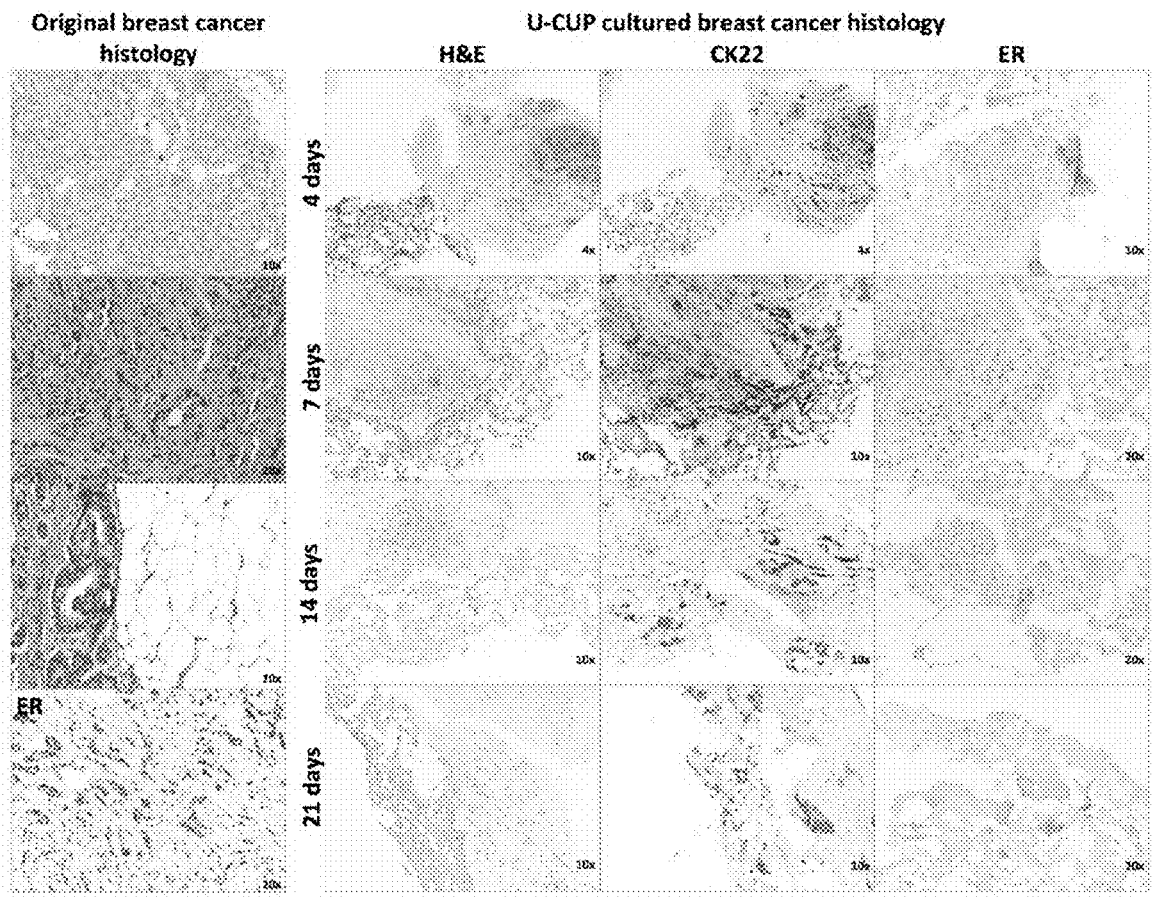

FIG. 12 shows the result of a third example for human Luminal A Breast Cancer. Thereby, essentially the same or similar methods and procedures are applied as described hereinbefore in connection with the second example directed to colorectal cancer tissue. However, in contrast to the colorectal cancer tissue example or to at least some samples thereof described hereinbefore, in the third example, the breast cancer tissue does not undergo any cleaning procedure, the breast cancer tissue is not pre-digested, the medium does not contain the antibiotics cocktail as specified above and no medium change as specified for some samples of colorectal cancer above is performed.

Luminal A breast cancer is defined as estrogen receptor (ER) positive, progesterone receptor (PR) positive, human epidermal growth factor receptor 2 (HER2) negative and with few proliferating tumor cells (low % of Ki67 positive cells). This type of tumor requires estrogen as growth factor for its survival and expansion. The downsized tissue or tissue chunks are cultured in a medium containing 10% of human autologous serum (AS), therefore receiving all the growth factors comprising the estrogen. The autologous serum (AS) is prepared by collecting a total blood sample from the tumor tissue related patient with a syringe without addition of anticoagulants; centrifuging the blood at 2600 g for 30 minutes and at 4° C.; and collecting the supernatant defined as AS. The column on the left shows H&E of freshly isolated primary Luminal A Breast Cancer and the ER staining. It important to notice that glandular-like structures observable in primary tissue are also visible in the H&E of bioreactor engineered tissue. To notice, the cells within the tumor tissue start to invade the scaffold from day 7. Epithelial tumor cells are maintained until the latest time point as shown by positive staining for CK22 (pan cytokeratin for the identification of epithelial cells). Instead, ER expression is loss at day 14.

After several experiments (9 specimens tested), the tissue chunks start to grow in the scaffold at 7 days of culture, forming glandular structures similar to in vivo tumor tissue. At the latest time point, 21 days, more cells were detectable in the scaffold, instead in the inner part of the chunks there were an increase of apoptotic cells.

The estrogen supplementation effect on in vitro culture is evaluated. Thereby, the aim is to understand if an extra supplementation of exogenous estrogen (2-Estradiol, Sigma-Aldrich, E2758, 200 ng/mL) can promote a better survival and proliferation of the tissue compare to the control (only the amount of estrogen present in the autologous serum). The data obtained do not show any particular difference between the tumor chunks with estrogen supplementation (E+) or without (E−).

Figure 13:
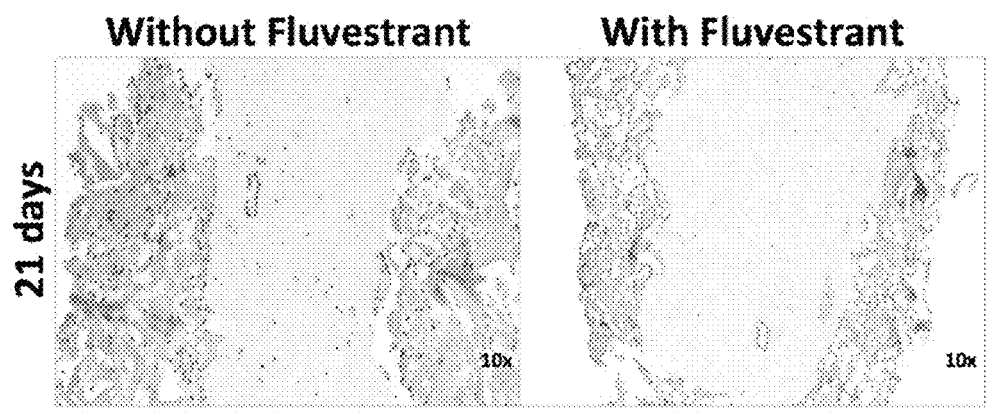

The anti-estrogen receptor drug effect on in vitro culture is also evaluated and shown in FIG. 13. The aim is to verify the possibility to perform a drug test on in vitro culture tumor specimen as a proof of concept for personalized medicine. As a drug, Fulvestrant (Sigma 14409)—a selective estrogen receptor down-regulator (SERD)—is chosen due to its long half-life (in human is 40 days) and because it is regularly used in clinic (Drug concentration to use: 100 nM (In-vitro test using ER-positive breast cancer cell lines: MCF-7, T47D, BT474 and MDA-MB-361. 7 days of treatment). The drug is added at the beginning of the bioreactor culture (day 0). As can be clearly seen in FIG. 13, there is an effect of the Fulvestrant treatment.

One important component of the tumor microenvironment is represented by the tumor infiltrating lymphocytes (TILs) that for some tumor types plays an important role by determining the patient prognosis and it is gaining a major attention in the so called cancer immune-therapy. By using PHA (Phytohemagglutinin), TILs are stimulated in their metabolic and proliferative activity, in order to understand if it was possible their stimulation inside the in vitro cultured tumor chunks. The PHA (1 ng/mL) is added at the beginning of the bioreactor culture (day 0).

Figure 14:
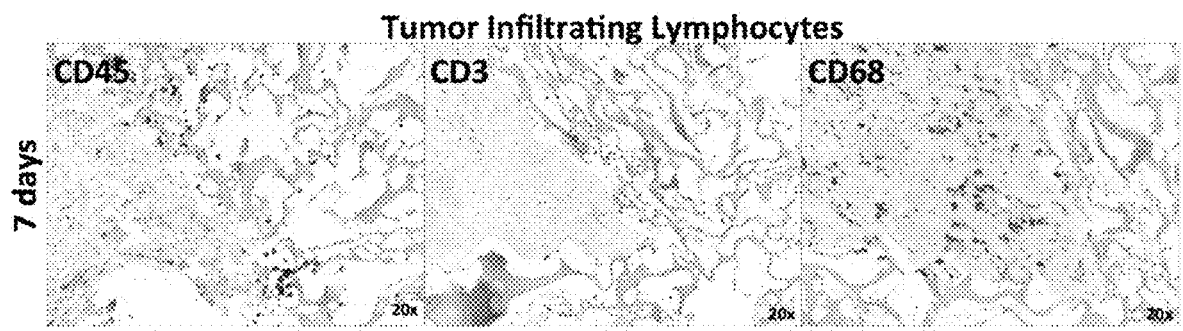

As shown in FIG. 14, at 7 days, the presence of TILs is still detectable with the CD3 positive T-cell mainly in the scaffold instead the macrophages CD68 cells still in the tissue. These raise the possibility to study immunological question or test cancer immunotherapies on in vitro cultured tumor specimens.

Based on the second example and its results prospects of use of the 3D perfusion bioreactor described in WO 2013/182574 A1 can be used for: testing promising pathways in tumor biology and immunology in vitro; as a tool to increment tumor-take for PDX (patient derived xenograft); as a pre-clinical in-vitro model for validation of putative new drugs; after HCS for: classic 2D tests or innovative 3D tests, and before animal experiments: for personalized medicine (PM) by expansion of primary tumor cells and for short time expansion or maintenance of live tissue.

While the invention has been illustrated and described in detail in the drawings and foregoing description, such illustration and description are to be considered illustrative or exemplary and not restrictive. It will be understood that changes and modifications may be made by those of ordinary skill within the scope and spirit of the following claims.

In particular, the present invention covers further embodiments with any combination of features from different embodiments described above and below.

The invention also covers all further features shown in the FIGS. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims ort the exemplary embodiments as well as subject matter comprising said features.

Furthermore, in the claims the word "comprising" does not exclude other elements or steps, and the indefinite article "a" or "an" does not exclude a plurality. A single unit or step may fulfill the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Any reference signs in the claims should not be construed as limiting the scope.

The invention claimed is:

1. A method of in vitro culturing or expanding human or animal tissue, comprising:
    obtaining a sample of human or animal tissue;
    downsizing tissue of the sample;
    generating an assembly by placing the downsized tissue on a scaffold or hydrogel;
    arranging the assembly inside a culture chamber of a 3D perfusion system; and
    perfusing the assembly in the 3D perfusion system for a predefined time.

2. The method according to claim 1, wherein downsizing the tissue comprises mechanically pre-treating the tissue.

3. The method according to claim 1, wherein downsizing the tissue comprises enzymatically pre-treating the tissue.

4. The method according to claim 1, further comprising: cleaning the tissue before generating the assembly.

5. The method according to claim 4, wherein cleaning the tissue comprises washing the tissue.

6. The method according to claim 4, wherein cleaning the tissue comprises anti-septic treatment.

7. The method according to claim 1, wherein generating the assembly comprises arranging a grid on one side of the scaffold or hydrogel and a further grid on the other side of the scaffold or hydrogel.

8. The method according to claim 7, wherein generating the assembly further comprises fixing the grid and scaffold or hydrogel together with a ring.

9. The method according to claim 1, wherein generating the assembly comprises placing the downsized tissue between two scaffolds such that the assembly is a sandwich assembly.

10. The method according to claim 1, wherein inside the 3D perfusion system the assembly is directly perfused.

11. The method according to claim 1, wherein the assembly in the 3D perfusion system is perfused in alternate directions.

12. The method according to claim 1, wherein the scaffold is coated with extracellular matrix proteins.

13. The method according to claim 1, wherein the scaffold is a porous biomaterial.

14. A method of testing efficacy of a tumor or cancer treatment, comprising:
    obtaining tumor or cancer tissue from the tumor or cancer of a patient;
    culturing the tumor or cancer tissue in a method according to claim 1;
    applying a first treatment suitable for treating tumor or cancer patients, or combinations thereof, to the cultured tumor or cancer tissue;
    monitoring changes in the growth, viability, and/or volume of the tumor or cancer tissue treated by the first treatment; and
    evaluating efficacy of the first treatment for the monitored tumor or cancer tissue.

15. The method according to claim 14, further comprising:
    obtaining further tumor or cancer tissue from the tumor or cancer of the patient;
    culturing the further tumor or cancer tissue in the method according to claim 1;
    applying a second treatment suitable for treating the tumor or cancer patients, or combinations thereof, to the further tumor or cancer tissue;
    monitoring changes in the growth, viability, and/or volume of the further tumor or cancer tissue; and
    selecting the first treatment or the second treatment as an in vivo treatment, by evaluating efficacy of the first treatment for the monitored tumor or cancer tissue and efficacy of the second treatment for the monitored further tumor or cancer tissue.

16. The method according to claim 15, wherein the first treatment comprises provision of a first substance to the tumor or cancer tissue and the second treatment comprises provision of a second substance to the further tumor or cancer tissue.

17. The method according to claim 15, wherein the first treatment comprises a first dosage regimen and the second treatment comprises a second dosage regimen.

18. A method of enriching cells of a cell type from human or animal tumor tissue comprising multiple cell types, the method comprising:
    comparing plural perfusion media with regard to their capacities of propagating the cells of the cell type;
    identifying a preferred perfusion medium from the plural perfusion media for propagating the cells of the cell type;
    selecting the preferred perfusion medium for perfusing the assembly in the 3D perfusion system;
    culturing the tumor tissue in a method according to claim 1 for a predefined time period using the preferred perfusion medium; and
    isolating the cultured cells of the cell type from the tumor tissue.

* * * * *